(12) United States Patent
Gapontsev et al.

(10) Patent No.: US 9,921,168 B2
(45) Date of Patent: Mar. 20, 2018

(54) METHOD AND SYSTEM FOR MONITORING OUTPUT OF HIGH POWER FIBER LASER SYSTEM

(71) Applicants: Valentin Gapontsev, Worcester, MA (US); Yuri Grapov, Sutton, MA (US); Michael Digiantommaso, Sutton, MA (US)

(72) Inventors: Valentin Gapontsev, Worcester, MA (US); Yuri Grapov, Sutton, MA (US); Michael Digiantommaso, Sutton, MA (US)

(73) Assignee: IPG PHOTONICS CORPORATION, Oxford, MA (US)

( * ) Notice: Subject to any disclaimer, the term of this patent is extended or adjusted under 35 U.S.C. 154(b) by 706 days.

(21) Appl. No.: 13/896,971

(22) Filed: May 17, 2013

(65) Prior Publication Data

US 2014/0339209 A1    Nov. 20, 2014

Related U.S. Application Data

(63) Continuation of application No. PCT/US2010/057796, filed on Nov. 23, 2010.

(51) Int. Cl.
   *B23K 26/30*      (2014.01)
   *G01N 21/958*     (2006.01)
   *B23K 26/70*      (2014.01)

(52) U.S. Cl.
   CPC ......... *G01N 21/958* (2013.01); *B23K 26/706* (2015.10); *B23K 26/707* (2015.10)

(58) Field of Classification Search
   CPC .. B23K 26/427; B23K 26/428; B23K 26/706; B23K 26/707; G01N 21/958
   USPC ............ 219/121.67, 121.81, 121.83, 121.84, 219/130.01; 359/362, 673, 813, 823, 830
   See application file for complete search history.

(56) References Cited

U.S. PATENT DOCUMENTS

| 2005/0018264 | A1* | 1/2005 | Benedict | G02B 26/10 359/196.1 |
| 2006/0186325 | A1* | 8/2006 | Johnston | G02B 6/262 250/234 |
| 2007/0114444 | A1* | 5/2007 | Reid | G01J 3/10 250/459.1 |
| 2009/0028407 | A1* | 1/2009 | Seibel | A61B 1/0008 382/131 |

(Continued)

FOREIGN PATENT DOCUMENTS

WO    WO 2012036664 A1 *  3/2012  ........ B23K 26/0608

*Primary Examiner* — Thien S Tran
(74) *Attorney, Agent, or Firm* — Yuri B. Kateshov, Esq.; Timothy J. King, Esq.

(57) ABSTRACT

The disclosure is a method and system for monitoring the condition of an optical protective component in a laser system associated with a data processor. In one embodiment, the method begins with directing light from the process head of a laser through the optical protective component onto a workpiece. A return light via the workpiece causes light signals coupled through the protective component and into to a fiber which extends proximate the protective component and thereafter flexibly to a sensor. The sensed signals allow monitoring the condition of the protective component during use. The method and system is operative for use with optical protective elements downstream of the process head.

20 Claims, 7 Drawing Sheets

(56) References Cited

U.S. PATENT DOCUMENTS

2014/0346330 A1* 11/2014 Blomster .............. G01J 1/4257
250/227.11

* cited by examiner

METHOD AND SYSTEM FOR MONITORING OUTPUT OF HIGH POWER FIBER LASER SYSTEM

BACKGROUND OF THE DISCLOSURE

1. Field of the Disclosure

The present disclosure relates to a method and system for monitoring an output of fiber laser systems. More specifically, the disclosure provides a fiber extending along a protective component and coupling light therefrom to a distal sensor detecting the coupled return light to monitor a condition relative to an optimal profile.

2. Description of the Related Art

Conventionally, a laser-welding/laser cutting process is associated with the high power laser radiation and the formation of a melting bath on the surface of the workpiece to be laser-treated. As the surface melts, liquid metal drops or "splashes" tend to impinge upon downstream components of focusing optics configured to guide a laser beam along a light path towards the surface and cause damage. Particularly affected is a protective element or glass—the "last" optical element located along the downstream end of the light path (relative to the laser source).

Deformation of the protective glass detrimentally affects several factors of a laser system, including the effective light power of a laser beam incident upon the surface of the workpiece. One example is in U.S. Pat. No. 6,118,527 (Jurca), the entire contents of which are incorporated herein by reference. The '527 patent teaches a complex light-detecting system including an array of spaced LEDs, which are spaced from the circumference of a protective glass and pulse additional light through the protective glass to a corresponding array of sensors. Cracks and fractures of the protective glass are detected by the light emitted from the LEDs and received by the sensors which may have a short useful life. The deteriorated condition of the protective element may reduce the power of the laser output radiation and reduce the effectiveness of the process.

Accordingly, there is a need for an improved method and system for monitoring the condition of an optical protective component in a fiber laser system.

ASPECTS AND SUMMARY OF THE DISCLOSURE

The disclosed method and system satisfy this need. In particular, the integrity of an optical component configured to protect optical elements in a laser head and further upstream in a laser light-generated source is realized by providing a fiber along the periphery of the element. If the protective element is compromised, the fiber receives light and delivers it to a sensor for a reading. Depending on the reading, the laser radiation source mat or may not be shut down.

The above and other aspects, features and advantages of the present disclosure will become apparent from the following description read in conjunction with the accompanying drawings, in which like reference numerals designate the same elements.

DETAILED DESCRIPTION OF THE PREFERRED EMBODIMENTS

Reference will now be made in detail to several embodiments of the disclosure that are illustrated in the accompanying drawings. Wherever possible, same or similar reference numerals are used in the drawings and the description to refer to the same or like parts or steps. The drawings are in simplified form and are not to precise scale.

Figure 1:
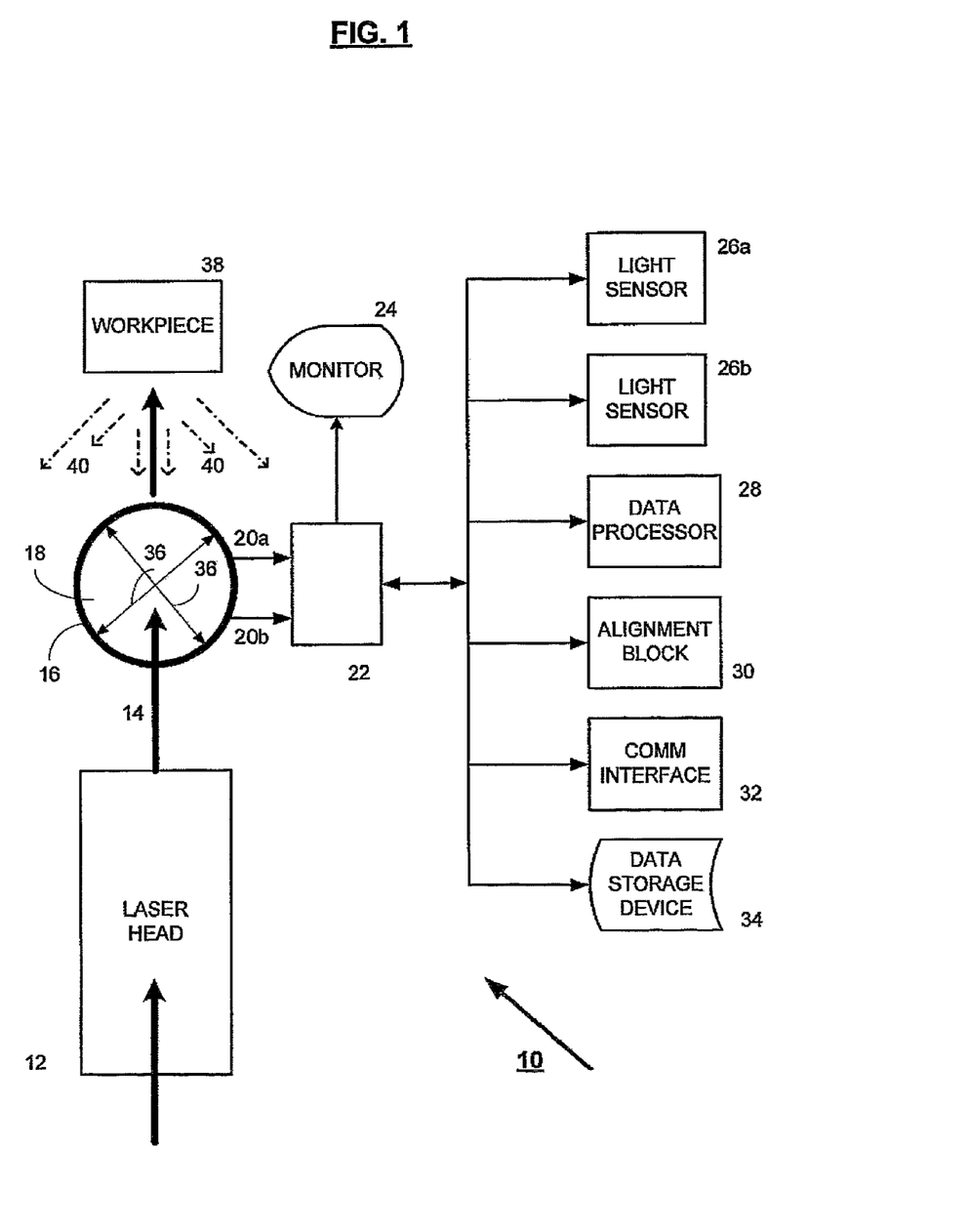
FIG. 1 is a block diagram of the system of the present disclosure.

Turning first to FIG. 1, there is shown a block diagram of a laser system 10 of the present disclosure. System 10 includes a laser process head 12 which receives a beam 14 propagating through a collimator and lens system towards an optical sealing window (OSW) 18 which serves as an optical component preventing damage to the former from backreflected light and debris. The OSW 18 is comprised of a material that operably allows beam 14 to pass substantially without distortion though before being directed downstream to a workpiece 38 for cutting, welding, or the like.

Thus, a direct beam of light from a laser source is directed through OSW 18 to workpiece 38 causing (optionally) a melted bath or molten region or weld (all not shown). In time, energetic (hot) metal splashes or debris from the workpiece reach and compromise OSW 18 causing cracks, debris accumulation and etc. If light is incident on deteriorated OSW 18, a portion thereof will be scattered and coupled into sensors 22, as disclosed below. Accordingly, the light reaching sensors 22 is further referred to as a return light 36 which has two sources: (a) the light 40 back reflected from workpiece 38 and (b) the direct incident laser beam.

In sum, there may be physical degradation (refractive index changes) in OSW 18. This degradation results in damaged regions on OSW 18 that scatter return light 36 propagating in multiple directions. One portion of the scattered light propagates towards the outer edge or periphery of OSW 18. Still another portion propagates upstream from OSW 18.

The outer edge or periphery of OSW 18 may be in any convenient shape. An optical fiber 16 wraps at least partially around OSW 18. Optical fiber 16 receives coupled return light 36 and guides the coupled light therealong toward ends 20a, 20b and then to end sensors (shown later) being operative to measure light power. Optionally optical fiber 16 can cover any portion of the edge of OSW 18 before terminal ends 20a, 20b are operably routed into the sensors. Both the profile of optical fiber 16 and an edge profile of OSW 18 can be in any operable shape or surface contact geometry effective to couple return light 36 from OSW 18 into fiber 16. Light guiding coatings (not shown) may be applied to the OSW 18/fiber 16 connection to aid coupling.

A housing 22 may enclose electronic system links to a number of peripherals. Peripherals can be either required (such as light sensors 26a and 26b, an alignment block 30, or a data processor 28), or can be optional (such as a monitor 24, a communications interface 32, or a data storage device 34) depending upon non-limiting system requirements or data transfer capabilities.

An alignment block control 30 operably directs light emanating from terminal ends 20a and 20b to sensors 26a and 26b. Data from sensors 26a and 26b can be processed locally or remotely at a data processor (not shown, but an example is an electronically linked remote computer data processor). An electronic report can be generated in respect of the readings by utilizing a report formatting routine and directing such data to a printer, a monitor 24, a communications link 32, or to a data storage device 34.

Light coupled through optical fiber 16 to light sensors 26a and 26b is read for a duration of time to create a unit of measure. Data processor 28 assigns a value to the unit of measure to create a reading; and, the reading is compared with a predetermined and adjustable desired profile range. If the reading is outside the profile range, an alarm signal is generated. The alarm signal can be given in any conventional manner such as an audible, electronic, or visual signal. Additionally, the alarm can be in the form of an action, wherein if laser system 10 determines that the reading is outside an acceptable profile range and then a shuts down action is taken, pending a maintenance check or replacement of OSW 18. However, if a reading is within the predetermined profile range, then no action is taken, data is updated, and a subsequent reading is awaited.

There are a number of causes for a reading to be outside the acceptable profile range. Light power, dirt, damage, or debris from return elements 40, or a less than sterile environment, physical changes in OSW 18 even if at an atomic level can greatly affect the integrity of a high powered light beam 14. Ultimately, degradation of OSW 18 (i.e., pitting or chemical breakdown) leads to dangerous conditions and substantial damage to laser head 12 and the operating environment.

Figure 2:
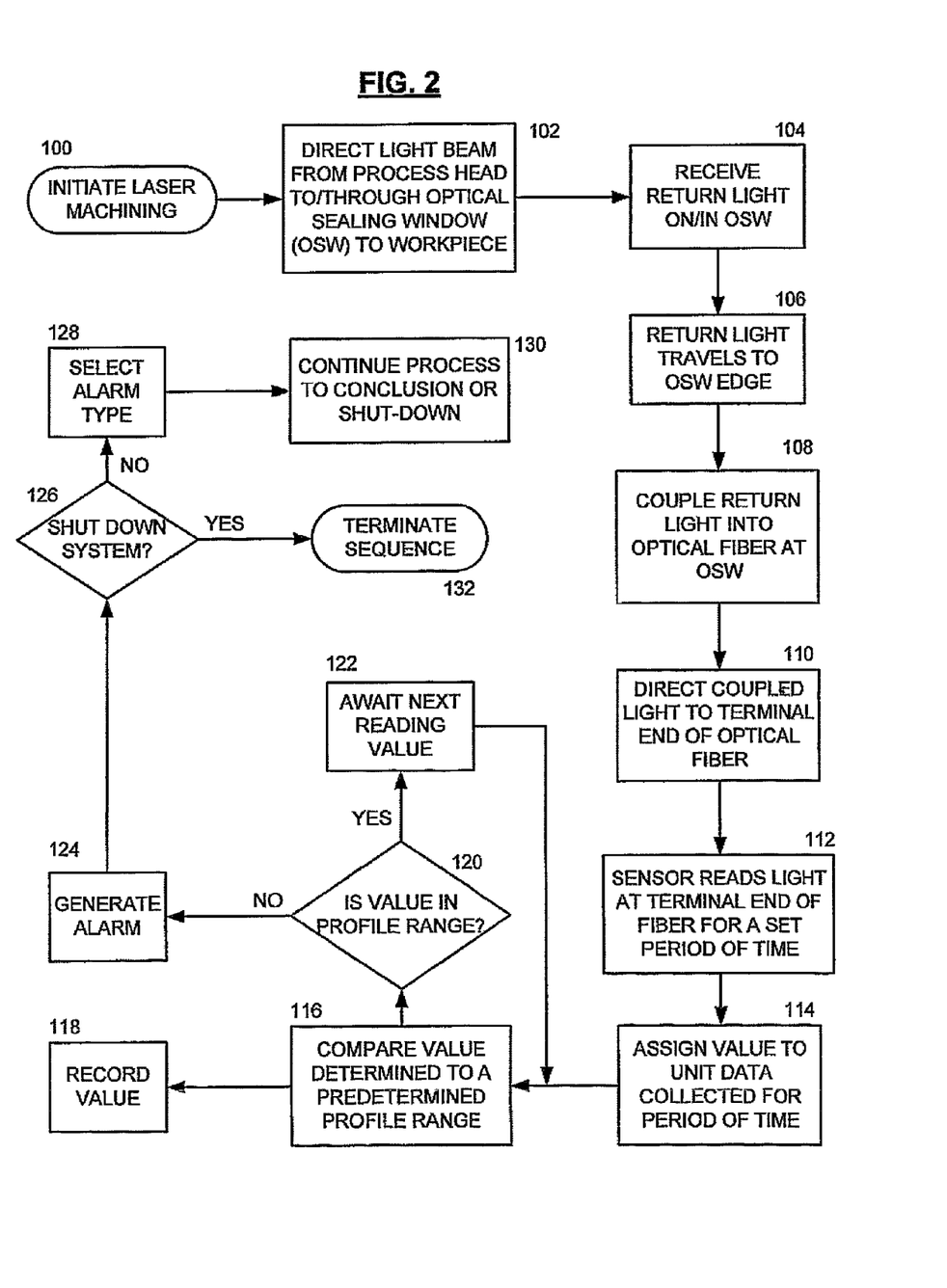
FIG. 2 is a flowchart of the method of the present disclosure.

Turning then to FIG. 2 there is shown a flowchart of an exemplary method of the present disclosure. The method flow begins at step 100 when laser system 10 is activated for a machining routine. After initialization, the flow advances to step 102 where a light beam is directed from the process head of the laser system through a lens and then through optical sealing window (OSW).

In working the workpiece, return light can be directed onto the OSW at step 104. The return light, via reflection or splatter or other means discussed herein, create coupled return light 36 in OSW 18.

Encountering defects in OSW 18, a portion of return light 36 travels through the material of the OSW and arrives at its edge at step 106. From step 106, the light is coupled at step 108 by an optical fiber surrounding the OSW in whole or in part. The coupled light is directed, at step 110, along the length of the optical fiber until it reaches one of the fiber's terminal ends.

Upon arrival at the terminal end, the light is passed to light sensors by an alignment block element. At step 112, sensors read the arriving light for a set period of time to determine a unit of measure. From step 112, the flow advances to step 114 where a value is assigned to the data collected for the measured period of time. The flow then advances to step 116 where a system data processor compares the value determined to a predetermined profile range. The value is recorded at step 118. From step 116, the system data processor queries, at step 120, as to whether or not the compared value is within the acceptable profile range. If the response to the query is "YES", then the flow simply awaits a next reading value at step 122 and re-enters the flow in front of step 116. However, if the response to the query at step 120 is "NO", then the system generates an alarm at step 126.

In receiving an alarm prompt, the system queries, at step 126, as to whether or not the system is to be shut down. The response from the system will be determined based on the predetermined thresholds for the profile range. If the response to the query is "YES", then the flow advances to step 132 where the system is shut down for operable maintenance. However, if the response to the query at step 126 is "NO", then the flow advances to step 128 where an alarm type is selected.

The alarm type can be selected from among a number of options which may include: an audible alarm; a visual alarm; a null alarm (meaning nothing occurs); or, a report can be generated. These options can be selected individually or in groups depending upon the needs of the system. The selection will determine, at step 130, whether the process will continue or be shut-down.

Figure 3:
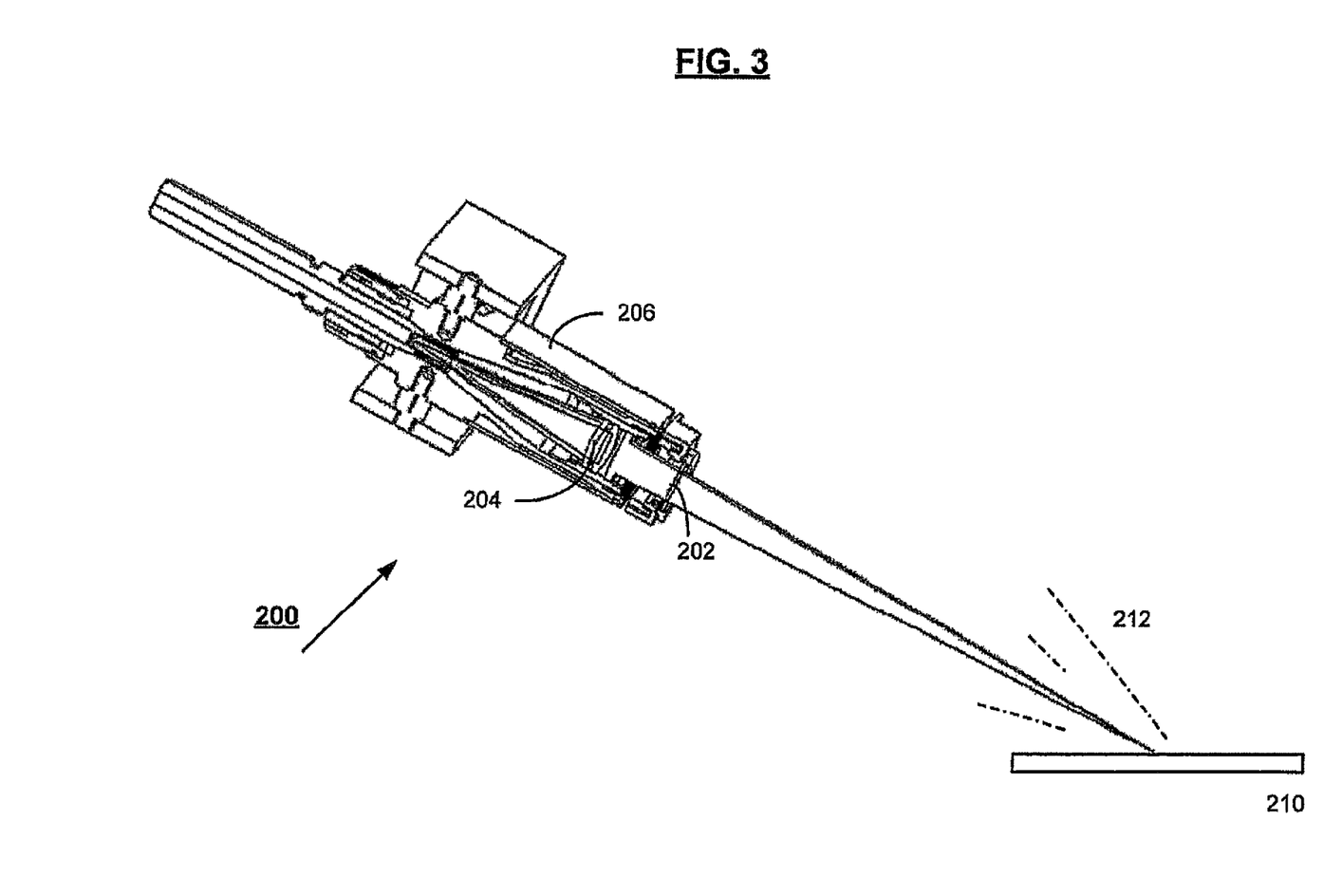
FIG. 3 is illustrative drawing of aspects of the proposed disclosure.

Perspective, FIGS. 3-7 illustrate the environment in which the OSW resides. FIG. 3 is schematic drawing of a laser system 200 of the present disclosure. System 200 has a process head 206 which directs a light beam downstream through a lens 204 before passing through an optical sealing window (OSW) assembly 202 as a protective optical component. The beam is directed to a workpiece 210 which may lie in a variety of planes. During the work or machining process being performed on workpiece 210, back splatter from debris or light 212 can be sent in the direction of the OSW assembly 202.

Figure 4:
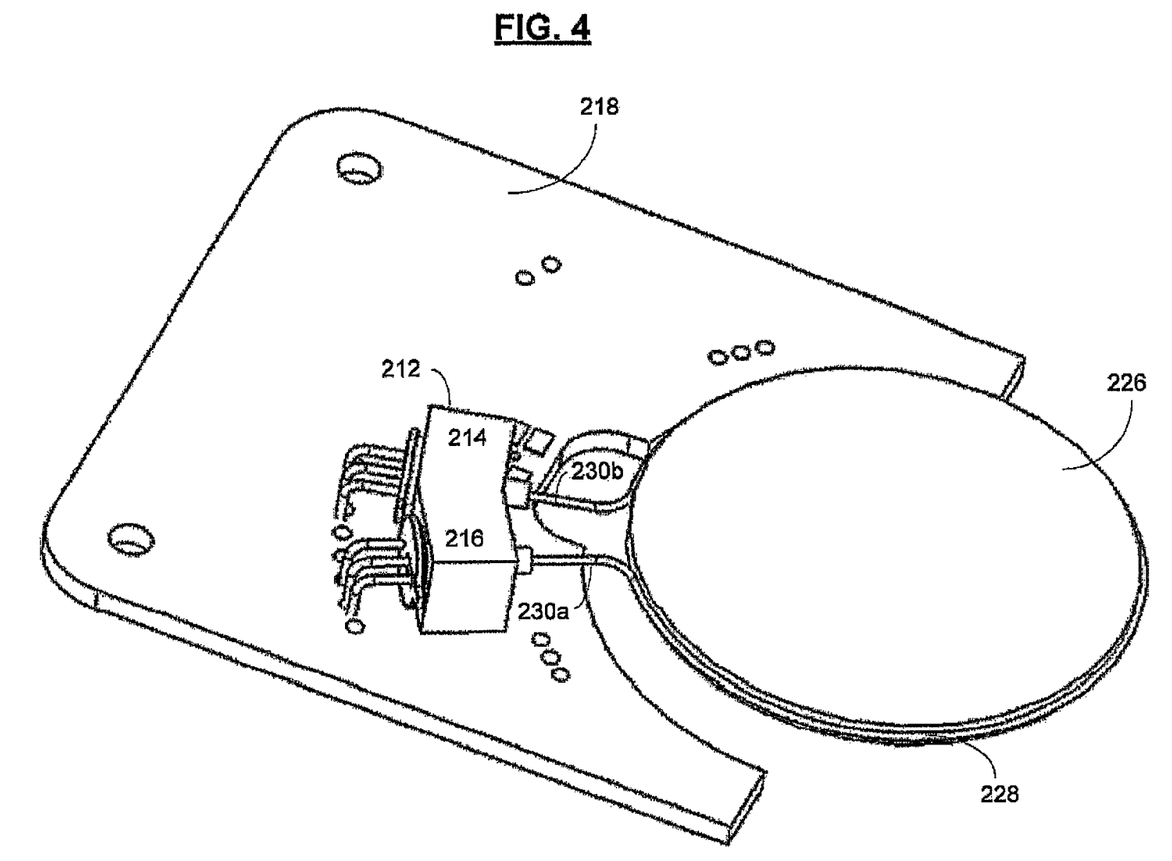
FIG. 4 is a schematic drawing of the optical sealing window (OSW) mounted to an associated printed circuit card and showing an optical fiber wrapped round the OSW.

FIG. 4 is a schematic of an optical sealing window (OSW) 226 mounted to an associated printed circuit card 218 and showing an optical fiber 228 wrapped at least in part about OSW 226 and flexibly terminating at ends 230a and 230b within the sub-assembly housing 212 at light sensors 214 and 216. Alternatively, fiber 228 may be supported by any mount located either coplanar with OW 228 or in planes not coinciding with the plane of OSW 226 because scattered light is not necessarily unidirectional, as known to one of ordinary skills.

Figure 5:
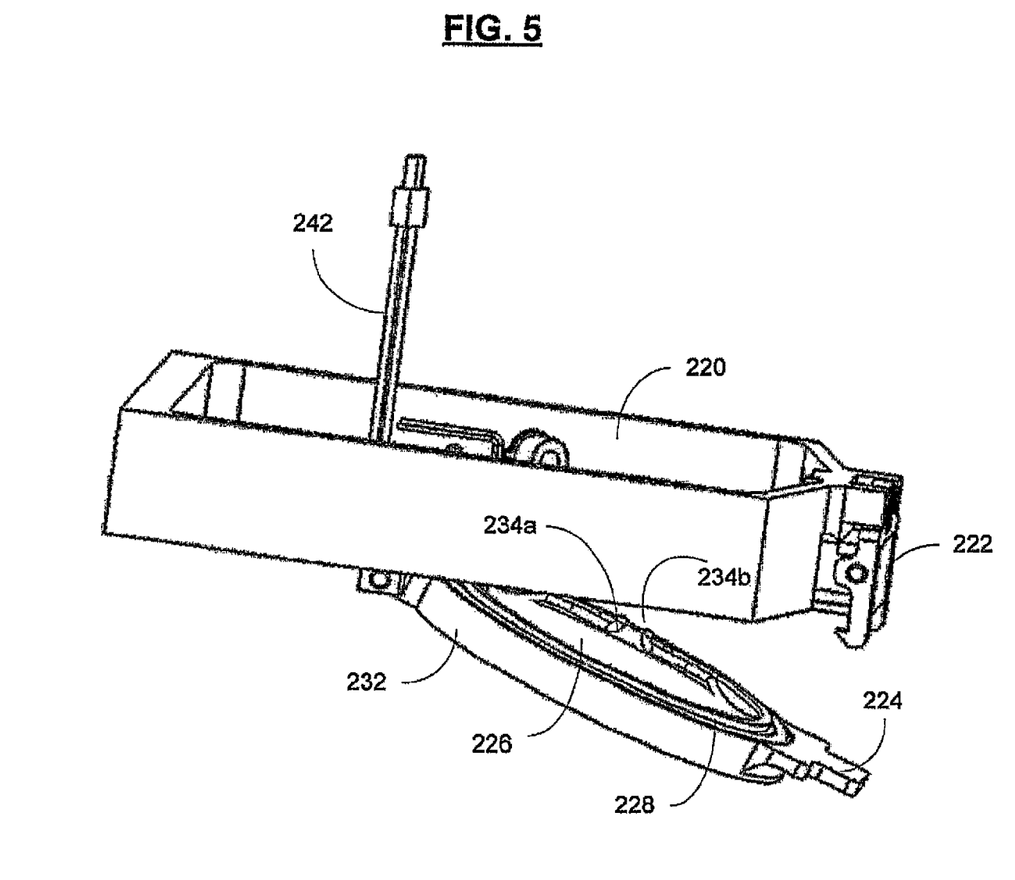
FIG. 5 is a prospective side view of the bracket retaining device that supports the OSW and associated printed circuit card. The OSW is tilted down in an unsealed disengaged position for illustration only.

FIG. 5 is a schematic view of bracket assembly 220 that supports OSW 226 and flexibly associated printed circuit card (not shown) and optical fiber 228. Spring clips 234a and 234b secure the OSW 226 in its frame 232. OSW 226 is tilted down to show its accessibility. OSW 226 with frame 232 can be latched to bracket retaining device 220 by mating a latch 222 with a tab 224. Data leads 242, which emanate from subassembly housing (not shown here), are shown in an upright position for mating with a downstream data assembly (not shown).

Figure 6:
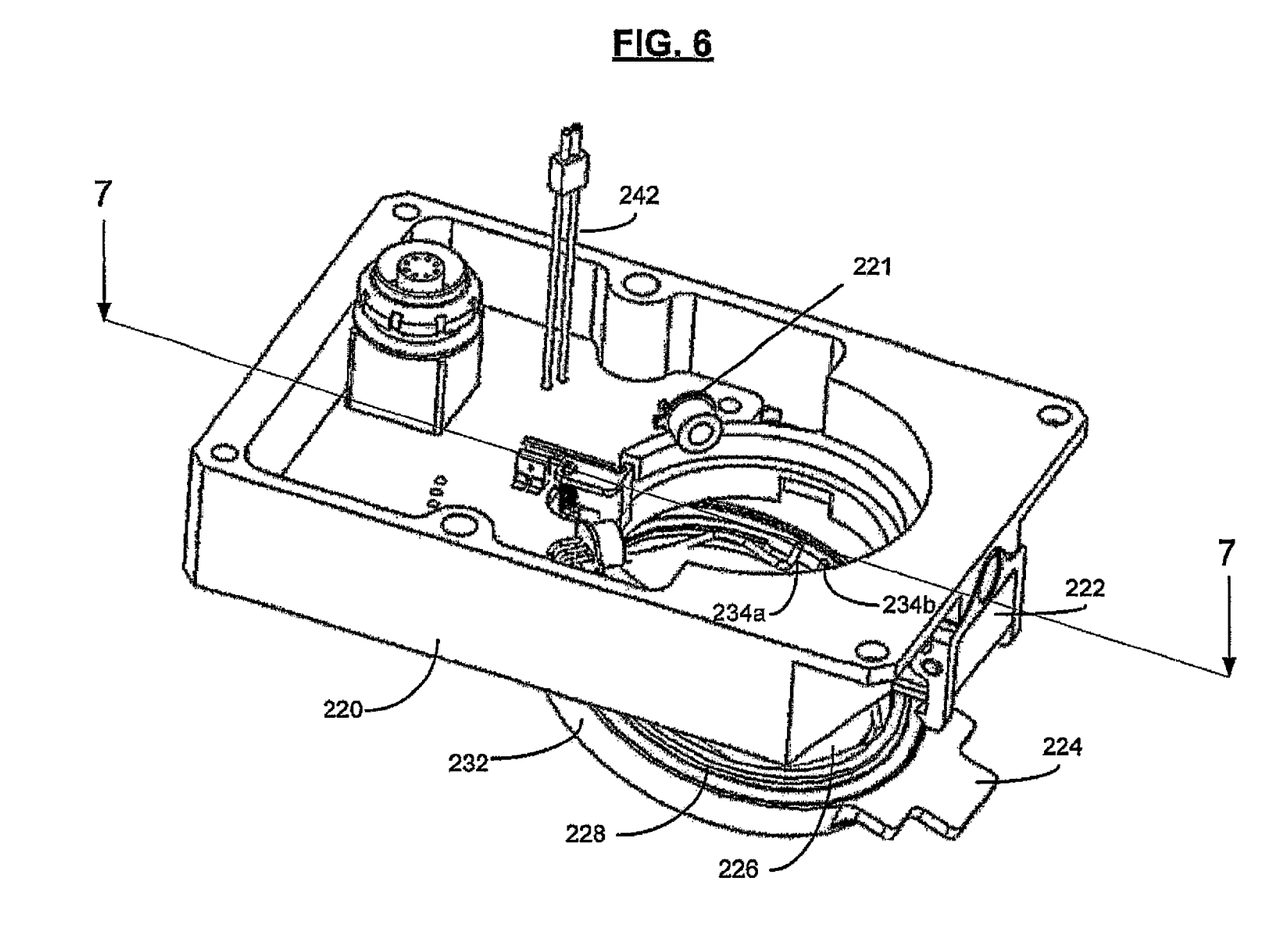
FIG. 6 is a prospective side view of the subassembly supporting the OSW as in FIG. 5.

FIG. 6 is a schematic of a perspective view of bracket assembly 220 supporting OSW 226 and being either the integral part of the laser head or detachable one. OSW 226 is tilted down to show its accessibility for maintenance, and illustrates the flexible connection enabled between optical fiber 228 and sensors 214, 216. Frame 232 is hinge latched to bracket assembly 220 by mating latch 222 with tab 224. Spring clip ends 234a and 234b secure OSW 226. Data leads 242 emanate from the subassembly housing 212 (not shown), are shown in an upright position for mating with a data assembly (not shown). Optical fiber 228, which directs light to the sensors, is sited on the periphery of OSW 226.

Also shown in FIG. 6 (and later in FIG. 7) are one or more reflected light sensors 221 positioned along the light path of laser light through the laser head onto OSW 226. Sensor 221 may be in any conventional laser sensor configuration and may be positioned in any operable position relative to OSW 226 to acquire reflected and/or scattered light returning from OSW 226 within the sealed bracket assembly 220 during operation. Multiple sensors 221 may be used in different positions. As shown, an optimal position for sensors 221 is on a support rim bounding the access region to OSW 226.

As will be understood, one or more sensors 221 generate signals relative to the amount of reflected and/or scattered light that is transmitted via data leads (not shown) to data processor 28 and related components in system 10, similar to the process shown in FIG. 1. In this way, system 10 may optionally and operably compare the value of scattered light from sensor 221 to the value of the return light noted earlier, and compare the difference to a predetermined profile range to generate a record and optionally an alarm, in a manner similar to the process shown in FIG. 1. In this way, system 10 may include an optional second sensor component 221 resulting in a useful comparison measurement to efficiently manage system 10.

Figure 7:
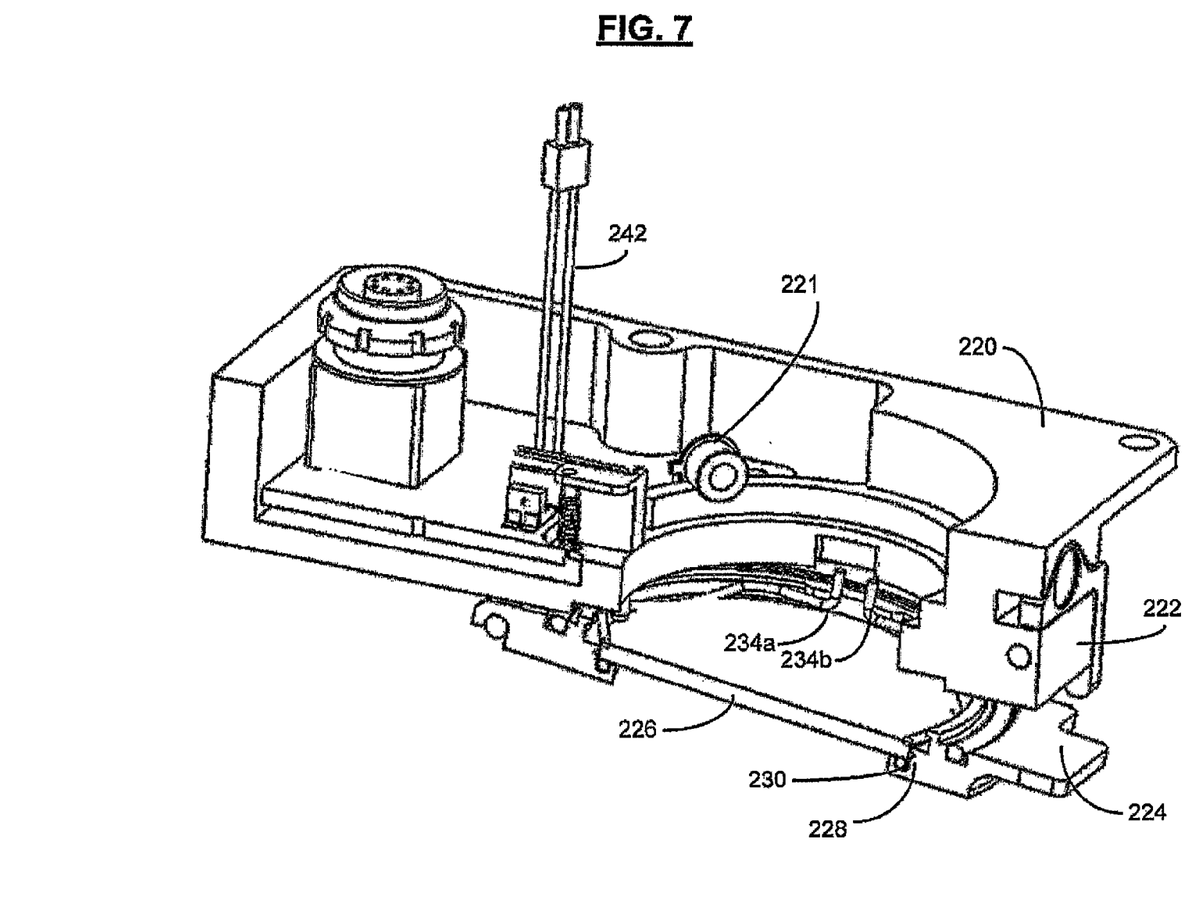
FIG. 7 is a sectional perspective view of the subassembly supporting the OSW along Section 7-7 in FIG. 6.

FIG. 7 is a cross sectional perspective view along line 7-7 in FIG. 6, and provides OSW 226 in a tilted down position. OSW 226 can be latched to bracket retaining device 220 by mating latch 222 with tab 224. Spring clip 234 has ends 234a and 234b and secures OSW 226 in frame 232. OSW 226 is cushioned in its frame by an elastomeric "O" ring 230 which sits under the outer edge of the OSW 226.

The current disclosure can be readily adapted to use as an OSW or optical protective component for a remote sensor in a laser manufacturing system, for example to protect an optical temperature sensor system proximate a workpiece.

In the claims, means or step-plus-function clauses are intended to cover the structures described or suggested herein as performing the recited function as well as functionally equivalent structures having different configurations. Having described at least one of the embodiments of the present disclosure with reference to the drawings, it is to be understood that the disclosure is not limited to these precise embodiments, and that various changes, and adaptations may be effected by one skilled in the art without departing from the scope or spirit of the disclosure as defined in the appended claims.

What is claimed is:

1. A method for operating a fiber laser system comprising the steps of:
   transmitting laser generated light propagating to and backreflected light propagating from an external worksite through an optical protective component mounted to an end of a laser head which faces the worksite;
   coupling return light including a portion of the backreflected light through the optical protective component into an optical fiber located proximate to the protective component;
   guiding the coupled return light along the optical fiber to a sensor which is operative to determine a measure of a light power thereof; and
   operating the laser system based upon a result of the determination of the light power.

2. The method of claim 1, wherein the optical fiber contacts a periphery of the optical protective component substantially continuously thereabout, and flexibly extends between the sensor and the optical protective component allowing an operable displacement thereof.

3. The method of claim 1 further comprising:
   transmitting the measure of the light power to a data processor;
   comparing the measure to a reference value thereby shutting down the laser system when the measured light power exceeds the reference value.

4. The method of claim 3, wherein the step of comparing is continuous until the measured light power exceeds the reference value.

5. The method of claim 2, wherein the sensor is substantially remote from the periphery of the optical protective component and at an end of the optical fiber.

6. The method of claim 1, wherein the return light further includes a portion of the forward propagating laser generated light.

7. The method of claim 1 further comprising:
   receiving the portion of return light in at least a second sensor secured upstream of the optical protective component in the laser head and generating a signal corresponding to a light power of the received return light; and
   operably guiding the signal along a data path to a data processor.

8. A system for monitoring an output of a fiber laser system, comprising:
   a process laser head guiding a direct laser beam along a path;
   an optical protective component mounted to a downstream end of the process head so as to receive and transmit the laser beam to a remote work site, and receive and transmit a backreflected light from the work site;
   an optical fiber located proximate to a periphery of the optical protective component so as to receive and guide return light selected from light portion consisting of the direct light, backreflected light and a combination of these; and
   a sensor coupled to the optical fiber and receiving the portion of the received light so as determine a measure of a light power thereof.

9. The system, according to claim 8, wherein the optical fiber contacts the periphery of the optical protective component substantially continuously thereabout, and flexibly extends between the sensor and the optical protective component.

10. The system of claim 8, further comprising:
    a data processor in operative communication with the sensor to receive the measure of the light power during a use of the system;
    a data storage device in operative communication with the data processor;
    data processing means in the data processor, the data processing means for assigning a value to the measure to create a reading; and for comparing the reading with a reference value stored in the data storage device; and
    the data processing unit being operative such that if the reading exceeds the reference value, then shutting down the system and replacing the protective element.

11. The system of claim 9, wherein the sensor is substantially remote from the periphery of the optical protective component, allowing relative displacement of the optical protective component and the sensor.

12. The system of claim 9 further comprising:
    a coating operative to contact the optical fiber and the periphery of the optical protective component substantially continuously thereabout, the coating being effective to aid the coupling of the return light from the periphery into the optical fiber.

13. The system of claim 8, wherein the return light includes scattered light generated upon propagating the forward and backreflected light through the optical protective component if the latter is damaged.

14. The system of claim 8 further comprising at least a second sensor secured upstream of the optical protective component in the process head, the second sensor being configured to receive another portion of the return light and operative to determine a measure of light power.

15. A laser process head operative to guide a laser generated beam to a worksite, the laser head comprising:
- an optical protective component pivotally mounted to a downstream end of a housing of the laser head along a light path;
- an optical fiber proximate a periphery of the optical protective component, the optical fiber configured to receive return light which includes at least a portion of light backreflected from the worksite along the light path; and
- a sensor optically coupled to the optical fiber and operative to determine a measure of a light power of the return light, wherein the protective component is pivotally displaced to an open position thereof for further replacement if the measured light power of the return light exceeds a reference value.

16. The laser head of claim 15 further comprising a bracket configured to support the protective component and coupled to the downstream end of the housing so as to pivot with the protective component between closed and the open positions.

17. The laser head of claim 15 further comprising at least a second sensor secured upstream of the optical protective component in the process head operative to determine the measure of light power.

18. The laser system of claim 16 further comprising a locking mechanism operative to lock the bracket to the housing upon pivoting the bracket to the closed position, the locking mechanism being configured with a latch mounted to one of the bracket and housing and a tab mounted on the other one of the housing and bracket, the tab and latch being configured to engage one another in the closed position of the bracket.

19. The laser system of claim 18 further comprising an elastomeric ring located between the bracket and configured to cushioning therebetween in the closed position of the frame.

20. The laser head of claim 15, wherein the return light includes scattered light generated upon propagating the laser generated light or light backreflected from the worksite or both through the optical protective component if the latter is damaged.

* * * * *